(12) United States Patent
Chen

(10) Patent No.: US 11,213,495 B2
(45) Date of Patent: Jan. 4, 2022

(54) METHOD AND COMPOSITION FOR DECREASING THE PSYCHOTOMIMETIC SIDE EFFECT AND ADDICTIVE DISORDER OF KETAMINE

(71) Applicants: NATIONAL HEALTH RESEARCH INSTITUTES, Zhunan Town (TW); Hsing-Jien Kung, Zhuhan Town (TW)

(72) Inventor: Hwei-Hsien Chen, Zhunan Town (TW)

(73) Assignee: NATIONAL HEALTH RESEARCH INSTITUTES, Miaoli County (TW)

(*) Notice: Subject to any disclaimer, the term of this patent is extended or adjusted under 35 U.S.C. 154(b) by 221 days.

(21) Appl. No.: 16/304,217

(22) PCT Filed: May 25, 2017

(86) PCT No.: PCT/US2017/034542
§ 371 (c)(1),
(2) Date: Nov. 23, 2018

(87) PCT Pub. No.: WO2017/205666
PCT Pub. Date: Nov. 30, 2017

(65) Prior Publication Data
US 2020/0069610 A1    Mar. 5, 2020

Related U.S. Application Data

(60) Provisional application No. 62/341,278, filed on May 25, 2016.

(51) Int. Cl.
| | |
|---|---|
| *A61K 31/135* | (2006.01) |
| *A61P 25/30* | (2006.01) |
| *A61P 25/24* | (2006.01) |
| *A61K 31/205* | (2006.01) |

(52) U.S. Cl.
CPC .......... *A61K 31/135* (2013.01); *A61K 31/205* (2013.01); *A61P 25/24* (2018.01); *A61P 25/30* (2018.01)

(58) Field of Classification Search
CPC ...... A61P 25/18; A61K 31/135; A61K 31/198
See application file for complete search history.

(56) References Cited

U.S. PATENT DOCUMENTS

| | | | |
|---|---|---|---|
| 2002/0035145 A1 | 3/2002 | Tsai et al. | |
| 2005/0250851 A1* | 11/2005 | Tsai | A61K 31/198 514/561 |
| 2007/0287753 A1 | 12/2007 | Charney et al. | |
| 2012/0041066 A1* | 2/2012 | Lombard | A61P 25/00 514/562 |

FOREIGN PATENT DOCUMENTS

CN        104352688 A      2/2015

OTHER PUBLICATIONS

Kim (Biomolecules and Therapeutics vol. 21 pp. 79-83 published 2013) (Year: 2013).*
Yang etal (Neuroscience Letter vol. 469 pp. 127-130 published 2010) (Year: 2010).*
Melo (Translational Psychiatry vol. 5 pp. e573—pp. 1-10, published 2015) (Year: 2015).*
Kim etal (Biomolecules and Therapeutics vol. 21 pp. 79-83 published 2013) (Year: 2013).*

* cited by examiner

Primary Examiner — Theodore R. Howell
Assistant Examiner — George W Kosturko
(74) Attorney, Agent, or Firm — Muncy, Geissler, Olds and Lowe, P.C.

(57) ABSTRACT

The present invention relates to a method for decreasing the psychotomimetic side effects and enhancing the antidepressant-like effects of ketamine by the combination of ketamine with a methylglycine derivative. The present invention also relates to a method for depression treatment comprising administrating ketamine combined with a methylglycine derivative. The present invention further provides a method for preventing or treating addictive disorders of ketamine by administrating a methylglycine derivative.

8 Claims, 18 Drawing Sheets

METHOD AND COMPOSITION FOR DECREASING THE PSYCHOTOMIMETIC SIDE EFFECT AND ADDICTIVE DISORDER OF KETAMINE

CROSS-REFERENCE TO RELATED APPLICATION

This application claims priority to U.S. Provisional Application No. 62/341,278, filed on May 25, 2016, the entire content of which is hereby incorporated by reference herein in its entirety.

FIELD OF THE INVENTION

The present invention relates to a method for decreasing the psychotomimetic side effects and addictive disorders of ketamine by using betaine or a betaine metabolite. Especially, the present invention relates to a method for depression treatment comprising administrating ketamine combined with betaine or a betaine metabolite N,N-dimethylglycine (DMG).

BACKGROUND OF THE INVENTION

Ketamine, a dissociative anesthetic, produces multiple effects on the central nervous system. Recently, accumulating evidence reveals that ketamine exerts rapid and lasting antidepressant effects (Koike et al., *Behav Brain Res* 224: 107-11, 2011; Maeng and Zarate, *Curr Psychiatry Rep.* 9:467-74 2007), particularly in treatment-resistant patients in clinical studies (Diamond et al., *Journal of psychopharmacology* 28:536-44, 2014; Kallmunzer et al., *Journal of neural transmission* 123:549-52, 2016; Messer et al., *Journal of neuropsychiatry and clinical neurosciences* 22:442-4, 2010; Singh et al. *The American journal of psychiatry* appiajp201616010037, 2016). These observations implicate that ketamine may exert its effects through different action sites and neural circuits.

Despite ketamine can induce a rapid onset of antidepressant effect, the adverse mental status associated with ketamine use including psychosis, dissociative, hallucinogenic, and amnesic effects (Krystal et al., *Arch Gen Psychiatry* 51: 199-214, 1994; Perry et al., *Psychopharmacology* (Berl) 192: 253-60, 2007), leads to discontinuation. Accordingly, research attempts have been focusing on developing new compounds with more specific rapid-acting antidepressant treatments but free of ketamine's adverse effects (Browne and Lucki, *Front Pharmacol* 4: 161, 2013; Burgdorf et al., Neuropsychopharmacology: official publication of the American College of Neuropsychopharmacology 38: 729-42, 2013). Alternatively, an adjunct treatment which can promote the therapeutic efficacy and concomitantly avoid the adverse effects of ketamine has also been considered (Chiu et al., *Int J Neuropsychopharmacol* 18: 1-13, 2015; Ibrahim et al., Neuropsychopharmacology: official publication of the American College of Neuropsychopharmacology 37: 1526-33, 2012).

The mechanisms underlying the antidepressant and psychosis-inducing effects of ketamine have been suggested to be associated with blockade of N-methyl-D-aspartate receptors (NMDARs). Numerous studies have shown that enhancing NMDAR function, via activation of glycine binding site or modulation of metabotropic glutamate receptors, represents a promising approach to reverse psychotomimetic effects of ketamine (Chan, *Psychopharmacology* (Berl) 198: 141-8, 2008; Krystal et al., *Psychopharmacology* 179: 303-9, 2005; Roberts et al., *Neuroreport* 21: 390-4, 2010; Yang et al., *Neurosci Lett* 469: 127-30, 2010).

Therefore, the present invention evaluated the effects of a methyl glycine derivative, betaine or its metabolite N,N-dimethylglycine (DMG), on promoting the antidepressant-like, but antagonizing the psychotomimetic effects of ketamine.

SUMMARY OF INVENTION

In the present invention, it is found that a methyl glycine derivative, betaine or its metabolite N,N-dimethylglycine (DMG), could antagonize ketamine's psychotomimetic effects, yet produce additive antidepressant-like effects with ketamine, suggesting that the methyl glycine derivative might have antipsychotic potential and be suitable as an add-on therapy to ketamine for patients with treatment-resistant depression.

Accordingly, in one aspect, the present invention relates to an additive anti-depressant composition comprising an effective amount of ketamine and a methyl glycine derivative carrying at least two methyl groups.

In certain embodiments of the present invention, the methyl glycine derivative is selected from betaine and a betaine metabolite. In other embodiments, the betaine metabolite is N,N-dimethylglycine (DMG).

In certain embodiments of the present invention, the composition is used for the treatment of depressive symptoms in a patient with schizophrenia. In other embodiments, the composition is used for reducing the psychotomimetic side effect of ketamine.

Preferably, the effective amount of ketamine used in the composition is lower than its individual dose for treating depression. Furthermore, the composition is used for preventing or treating the addictive disorder of ketamine.

In another aspect, the present invention relates to a method for treating depression in a subject with need thereof, comprising administrating an effective amount of ketamine combined with a methyl glycine derivative to the subject.

In certain embodiments, the subject is a schizophrenic patient with depression. In other embodiments, the subject is a patient with treatment-resistant depression.

BRIEF DESCRIPTION OF THE DRAWINGS

In FIG. 7A and FIG. 7B, the latency and the duration of loss of righting reflex were recorded, respectively. All values are expressed as the mean±SEM (n=7).

In FIG. 12A, spontaneous locomotor activity (habituated) was recorded for 2 hr. DMG (0, 30 and 100 mg/kg) administered at 120 min and ketamine (30 mg/kg) were given at 150 min and a Saline/Saline group was used as a control. In FIG. 12B, total distances after ketamine administration were measured for 30 min (B). All values are expressed as the mean±SEM (n=9/group). ***p<0.001 compared with the Saline/Saline, ##p<0.01, ####p<0.001 vs. Saline/Ketamine.

DETAILED DESCRIPTION OF THE INVENTION

Figure 1A:
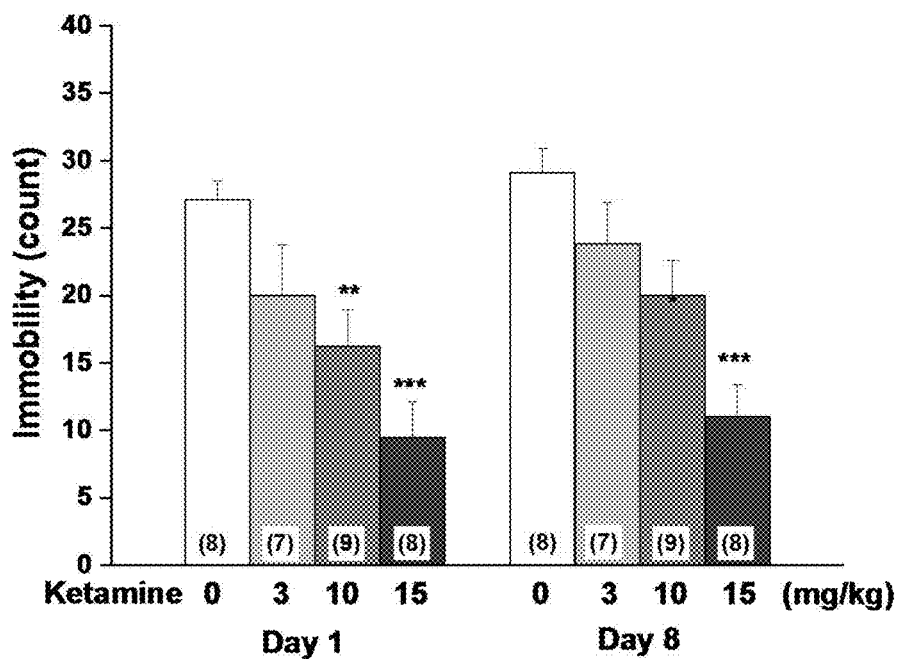
FIGS. 1A and 1B show the dose-dependent effects of ketamine and betaine on forced swimming test (FST) scored by time-sampling method. The acute and sustained effects of various doses of ketamine (3, 10, 15 mg/kg) and betaine (10, 20, 30 mg/kg) on FST were assessed on day 1(A) and 8 (B), respectively. All values are expressed as mean±SEM. *p<0.05, p<0.01, *p<0.001 compared with respective control.

As used herein, term "methyl glycine derivative" refers to a derivative of the amino acid glycine carrying at least two methyl group. Examples of methyl glycine derivative include betaine and a betaine metabolite N,N-dimethylglycine (DMG). Examples of methyl glycine derivative also include a pharmaceutically acceptable salt of betaine or N,N-dimethylglycine.

Ketamine (or RS-ketamine) is a racemic mixture containing equal parts of R-ketamine and S-ketamine. Therefore, as used herein, term "ketamine" refers to ketamine or an isomer thereof. The term "ketamine" should also include a pharmaceutically acceptable salt and an active metabolite of ketamine with similar antidepressant effects of ketamine.

The present invention provides a pharmaceutical composition for treating depression in a subject with need thereof comprising an effective amount of ketamine combined with a methyl glycine derivative. The antidepressant composition of present invention may be used to decrease the side effects of ketamine, maximize the therapeutic effectiveness of ketamine, and/or prevent or treat the addictive disorder of ketamine.

The term "treating" refers to application or administration of an effective amount of ketamine and/or a methyl glycine derivative to a subject suffering from depression or a psychotomimetic effect of ketamine, with the purpose to cure, remedy, relieve, alleviate, or ameliorate the disease or its symptom(s). "An effective amount" refers to the amount of ketamine combined with a methyl glycine derivative which is required to confer the desired effect on the subject. Effective amounts vary, as recognized by those skilled in the art, depending on route of administration, excipient usage, and the like.

For example, ketamine and a methyl glycine derivative can be administered to an animal (e.g., a mouse model) having depression or ketamine-induced impairments and its therapeutic effects are then assessed. Based on the results, an appropriate dosage range and administration route can also be determined. The animal dose should not be extrapolated to a human equivalent dose (HED) by a simple conversion based on body weight. The Food and Drug Administration has suggested that the extrapolation of animal dose to human dose is correctly performed only through normalization to BSA, which often is represented in $mg/m^2$. The human dose equivalent can be more appropriately calculated by using the formula: HED (mg/kg)=Animal dose (mg/kg) multiplied by Animal Km/Human Km.

The other characteristics and advantages of the present invention will be further illustrated and described in the following examples. The examples described herein are using for illustrations, not for limitations of the invention.

Materials and Methods

Animals

Male ICR mice (8-10 weeks, 30-45 g) were supplied from the BioLASCO Charles River Technology (Taiwan) and housed 4-6 per cage in a 12 h light/dark cycle with ad libitum access to water and food. Male Sprague-Dawley rats (300-350 g) were supplied from the BioLASCO Charles River Technology (Taiwan) and used for ketamine intravenous self administration. All experiments were carried out between 10:00 and 17:00 h and in accordance with the Republic of China animal protection law (Chapter III: Scientific Application of Animals) and approved by the Review Committee of the institutional animal care and use committees of Tzu Chi University and National Health Research Institutes, Taiwan.

Forced Swim Test (FST)

FST was conducted for two consecutive days. Mice were placed in a Plexiglas cylinder (33.5 cm height, 20 cm diameter) filled with 25±2° C. water to a height of 18-20 cm. For the first exposure, mice were placed in the water for 15 min (pre-test session) followed by 2 subsequently tests one week apart. Twenty-four hours later (day 1 test session), various doses of test drug (at 0, 30 and 100 mg/kg) was administered 30 min prior to the ketamine (10 mg/kg) or saline. Then, the mice were tested 30 min after ketamine injection which placed in the water again for a 6 min session (test session), the first 2 minutes has elapsed. Immobility was assigned when no additional activity was observed other than that required to keep the head above the water.

Prepulse Inhibition Test (PPI)

The PPI was operated as described in our previous work (Chan et al., 2012a). Briefly, the animals were initially moved from the home cage, weighed, and then placed into the restrainers in the SR-LAB (San Diego Instruments, San Diego, Calif., USA) acoustic startle chambers for 30-min habituation. The test drug (0, 30 and 100 mg/kg) was administered 30 min prior to ketamine (30 mg/kg) or saline injection. After administration of ketamine or saline, the experiment started with a 5-min adaptation period during which the animals were exposed to 67-dB background white noise, and this background noise was continued throughout the session. Then, the following adaptation period startle session began with five initial startle stimuli (120 dB bursts of white noise, 40 ms duration). After the first five initial stimuli, mice received five different trial types: pulse alone trials (120 dB bursts of white noise, 40 ms duration), three prepulse and pulse trials in which 76, 81, or 86 dB white noise bursts (9, 14, and 19 dB above background) of 20 ms duration preceded 120 dB pulse by 100 ms prepulse onset to pulse onset, and no-stimuli trials during which only background noise was applied. Each of these trial types was presented five times in randomized order. The inter trial interval was 7-23 s, and the test lasted 15 min in total. Prepulse inhibition was calculated as the percent inhibition of the startle amplitude evoked by the pulse alone: % PPI=(magnitude on pulse alone trial−magnitude on prepulse+pulse trial/magnitude on pulse alone trial)×100.

Rotarod Test

Motor coordination was examined using an automated rotarod device (Singa; Technology Co., Ltd, Taiwan) for a maximum of 6 mice. A computer recorded the latency to fall in seconds. During two-three days training period, the mice were first trained on the rotarod at a constant speed of 20 rotations per minute (rpm) until all of the mice were able to spend at least 3 min on the road. The test drug (0, 30 and 100 mg/kg) was administered 30 min prior to the ketamine (30 mg/kg) or saline injection. Then, the mice were tested 10, 15, 20, 25, and 30 min after ketamine injection.

Open Filed Test

To evaluate the effect of DMG on ketamine-induced locomotor hyperactivity, the animals were moved from the home cage, weighed and placed into an activity cage (Columbus Auto-Track System, Version 3.0 A, Columbus Institute, Columbus, Ohio, USA) for 2 hours. Thereafter, the test drug (0, 30, and 100 mg/kg) was given 30 min prior to ketamine (30 mg/kg) or saline. The distance (cm) traveled was recorded for totally 180 min. A 70% alcohol solution was used to clean the inner surface of all the testing apparatus between trials to remove any potentially interfering odors left by the previous mouse.

Novelty Suppressed Feeding Test (NSF)

NSF test consisted of food-depriving mice overnight (24 hours). The test drug (10, 20 and 30 mg/kg), ketamine (10 mg/kg) or saline was administered 1 h prior to the test. At the time of testing, a single food pellet placed in the middle of a novel environment (a test box 40×40×40 cm). The latency to start feeding was used as a measure for depressive-like or anxiety-like behavior.

Emergence Test

The emergence test was examined in a test box (35×35×30 cm) contained an aluminum cylinder (10 cm deep×6.5 cm diameter) located lengthwise along one wall, with the open end 10 cm from the corner. The test drug (0, 30 and 100 mg/kg) or ketamine (10 mg/kg) was administered 30 min prior to the test. Mice were placed into the cylinder and tested for 10 min and scored three behavioral parameters: the latency to leave the cylinder, the number of entries into the cylinder and the total time spent inside the cylinder.

Novel Location and Novel Object Recognition Tests

The novel location recognition test (NLRT) and novel object recognition test (NORT) were examined in a Plexiglas open field box (35×35×30 cm) located in a sound-attenuated room and illuminated with a 20-W light bulb. The novel location and novel object recognition procedure consisted of habituation, training, and retention sessions. Habituation was conducted in two consecutive daily sessions, during which each mouse was allowed to individually explore the box in the absence of objects for 20 min. The animal is then removed from the arena and placed in its home cage. During the sample phase, each animal was placed in the box, and after 5 min, two identical sample objects (A+A) were simultaneously introduced in two corners. Each animal was allowed to explore the objects for 5 min. An animal was considered to explore the object when its head was facing the object at a distance of approximately 1 cm or less between the head and object or when it was touching or sniffing the object. The time spent exploring each object was recorded using stopwatches by an experimenter blind to the treatment condition.

After the sample phase, the mice were immediately returned to their home cages. The novel location recognition test was conducted 30 min after the training session. The animals were returned to the same box as during the sample phase, and one of the two objects was replaced with a novel local corner (A+A') to test the location-based recognition memory. After 24 hours, novel object recognition test was performed. The mice are allowed to explore the open field with one identical sample object and a novel object to assess the novel object recognition memory (A+B). The animals were allowed to explore the box freely for 5 min, and the time spent exploring each object was recorded as described above. The objects and chambers were cleaned with 70% ethanol after each use. A preference index, a ratio of the amount of time spent exploring the original object or the novel location/object over the total time spent exploring both objects, was used to evaluate recognition memory. The test drug (0, 30, and 100 mg/kg) was administered 30 min prior to the ketamine (30 mg/kg) or saline. The sample phase was tested 30 min after ketamine administration.

Loss of Righting Reflex (LORR)

The test drug betaine (0, 300, and 600 mg/kg) or DMG (0, 100 and 300 mg/kg) was administered 30 min prior to the anesthetic doses of ketamine (100 mg/kg). Then, the mice were placed in a clean cage until the righting reflex was lost. They were then placed in the supine position until recovery and the onset and duration of the loss of righting reflex was recorded. Recovery of the righting reflex was defined as the ability to perform three successive rightings.

Social Interaction Test

This protocol was modified from the original social interaction test (Lin et al. 2010; Qiao et al. 2001). The social interaction between pairs of mice was examined in an open-field box (35×35×30 cm) under normal room lighting. The paired mice were randomly assigned from different home cages with the same drug treatment. The test drug (0, 100 and 300 mg/kg) was administered 30 min prior to the ketamine (30 mg/kg). Five minutes later, each pair of unfamiliar mice was placed in the apparatus for 10 min and the total time that a pair spent in social interaction and specific social interaction behaviors (sniffing the partner, following, mounting, and crawling under or over the partner) were recorded by an observer who was blind to the drug treatments.

Statistical Analyses

All of the data are expressed as mean±SEM. The data from rotarod test, the percentage of PPI and the novel location/object recognition test were analyzed by two-way repeated ANOVA with time, prepulse intensity and testing phase as the within subject factor, respectively. The data from the duration of loss of righting reflex, the immobility time during the forced swimming test, and total distance in locomotor activity test were analyzed by one-way ANOVA. The Student-Newman-Keuls test was used for post hoc comparisons. Multiple comparisons were performed using the Fisher's LSD test. $P<0.05$ was considered statistically significant.

EXAMPLES

Example 1

Betaine Promotes the Antidepressant-Like Effect of Ketamine

Figure 1B:
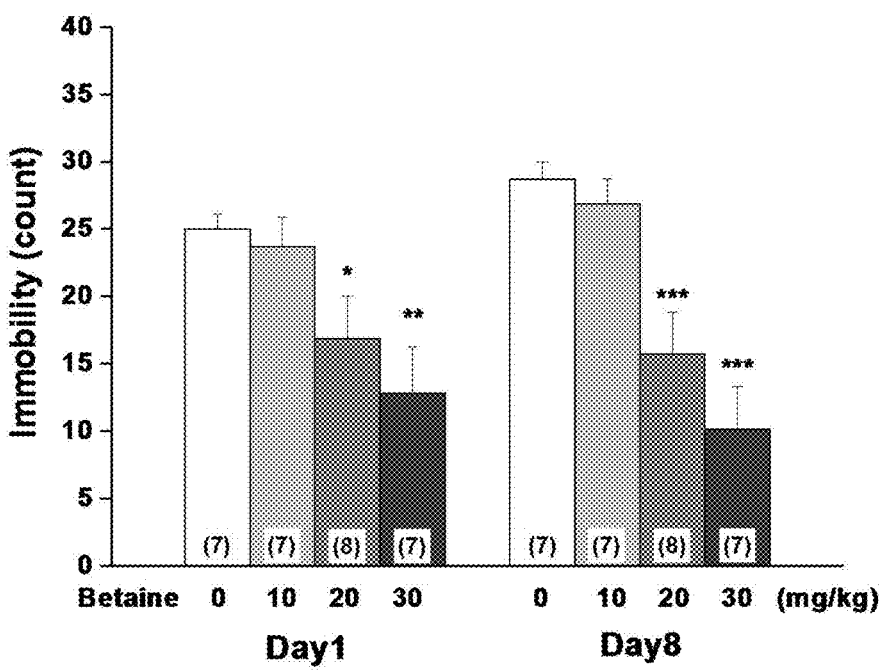

Dose-Dependent Effects of Ketamine and Betaine on FST Scored by Time-Sampling Method The acute and sustained effects of various doses of ketamine (3, 10, 15 mg/kg) and betaine (10, 20, 30 mg/kg) on FST were assessed on day 1 and 8, respectively (FIGS. 1A and 1B). A mixed-designed ANOVA on the count of immobility demonstrated significant main effects of ketamine ($F_{3, 28}=13.295$, $p<0.001$) and betaine ($F_{3, 25}=11.362$, $p<0.001$). There was no significant effect of test session or interaction. Post hoc comparisons showed that ketamine (3, 10, and 15 mg/kg) and betaine (20 and 30 mg/kg) significantly decreased the count of immobility.

Dose-Dependent Effects of Betaineon Novelty Suppressed Feeding Test

Figure 2A:
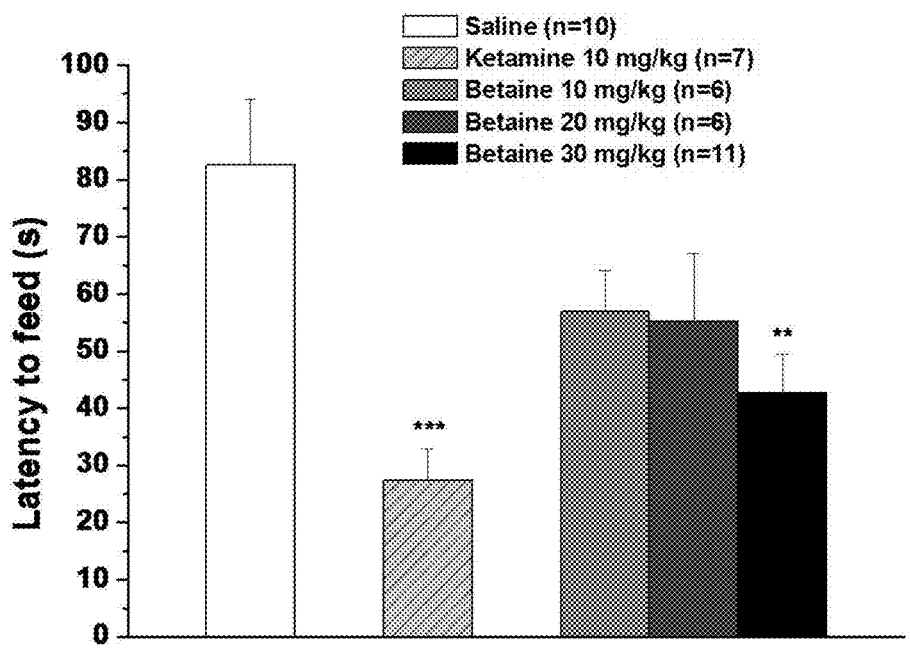
FIGS. 2A-2D show the effects of betaine and ketamine on the novelty suppressed feeding test (NSF) and emergence test. The animals were food restricted for 24 h. Betaine (0, 10, 20 and 30 mg/kg, i.p.) or ketamine (10 mg/kg) was administered 1 h prior to the test. The latency to feed was measured in NSF (A). The latency to leave the cylinder (B), the number of entries into the cylinder (C) and the total time spent inside the cylinder (D) were measured in the emergence test. All values are expressed as mean±SEM. *p<0.05, p<0.01, *p<0.001 compared with saline group.

The effects of ketamine (10 mg/kg) and betaine (10, 20, 30 mg/kg) on NSF were examined (FIG. 2A). One-way ANOVA revealed a significant treatment effect ($F_{4,35}=5.3$, $p<0.01$). Post hoc comparisons demonstrated that betaine (30 mg/kg) and ketamine (10 mg/kg) significantly reduced the latency to feed in the NSF compared with saline-treated mice.

Dose-Dependent Effects of Betaine on Emergence Test

Figure 2B:
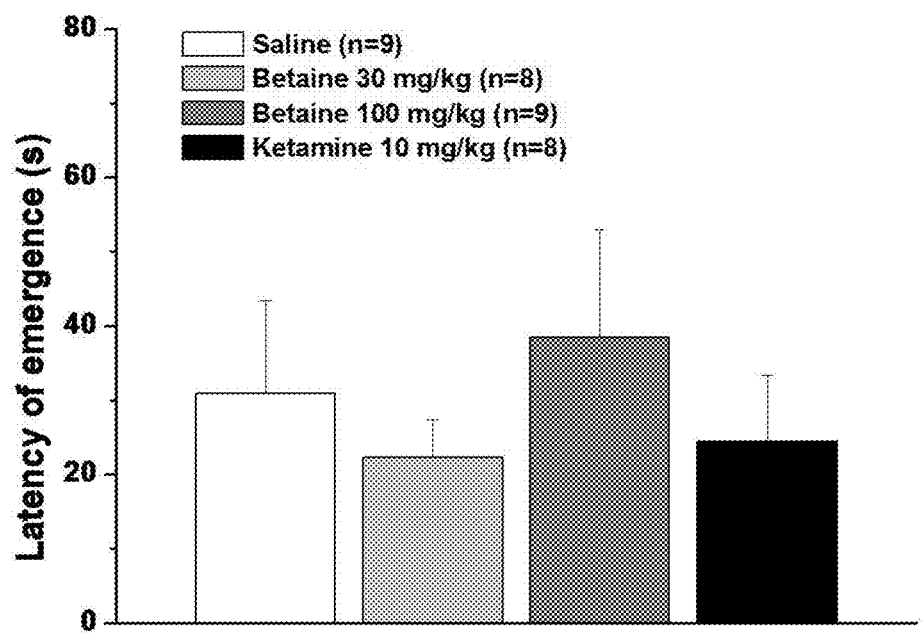
Figure 2C:
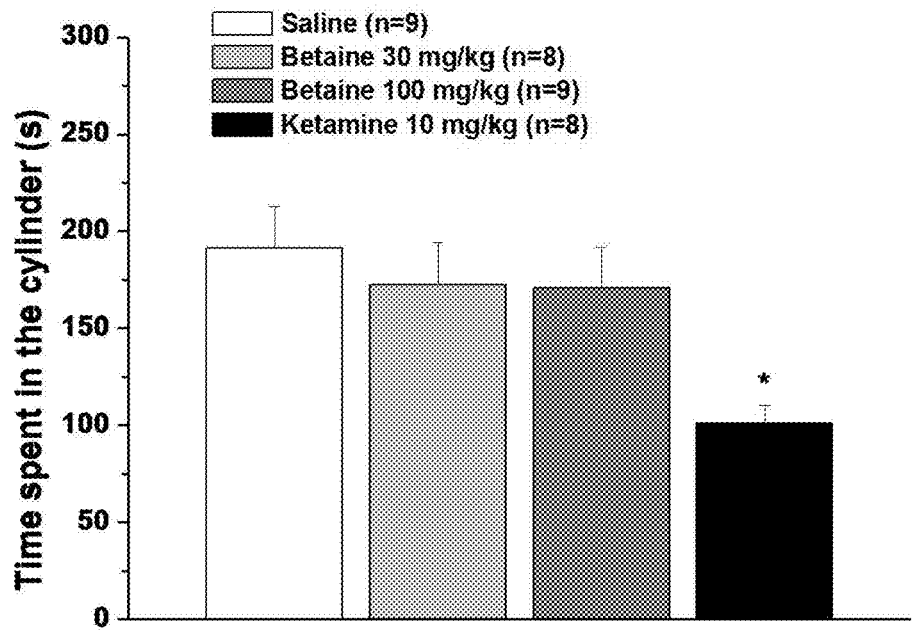
Figure 2D:
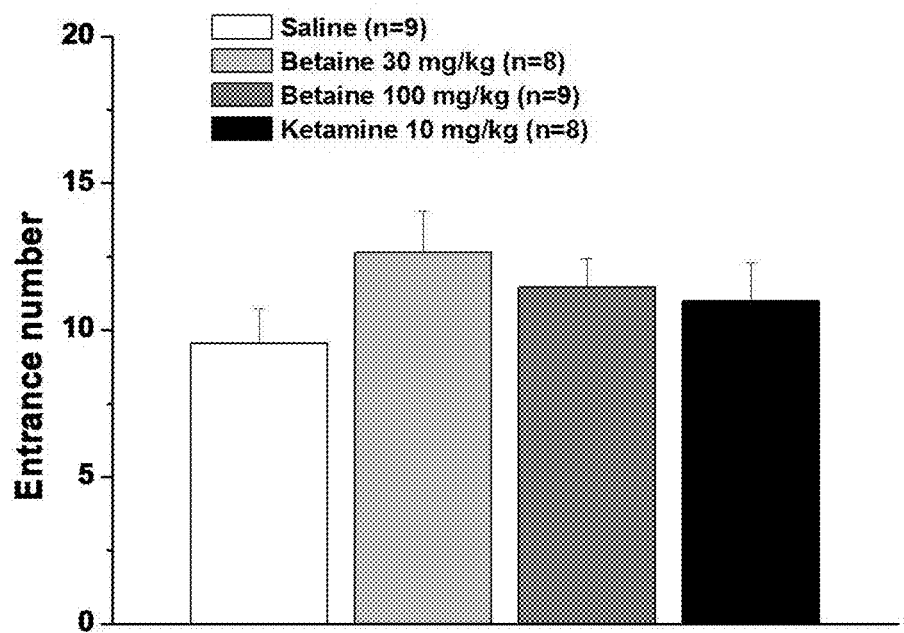

The effects of ketamine (10 mg/kg) and betaine (30 and 100 mg/kg) on emergence test were examined (FIG. 2B-D). One-way ANOVA revealed that there was a significant difference in the total time spent inside the cylinder ($F_{3, 30}=4.079$, $p<0.05$), but not in the latency to leave the cylinder ($F_{3, 30}=0.262$, $p=0.852$) and the number of entries into the cylinder ($F_{3, 30}=1.592$, $p<0.212$). Post hoc tests indicated that only ketamine significantly reduced the total time spent inside the cylinder.

In summary, betaine reduced the latency to feed in the NSF, supporting its antidepressant-like effect. Unlike ketamine, betaine did not show anxiolytic effect in the emergence test. These data administrated that betaine has an additive effect when combined with low dose of ketamine in the FST.

Effects of Ketamine and Betaine on the Duration of Immobility, Struggling and Swimming in FST This experiment included a control group and various doses of ketamine (3, 10, 15 mg/kg), betaine (10, 20, 30 mg/kg) and betaine (10, 20, 30 mg/kg) pretreatment prior to ketamine (fixed dose at 10 mg/kg). The duration of immobility, struggling and swimming was shown in FIG. 3. A mixed-design ANOVA revealed that there was a significant main effect of treatment on the duration of immobility ($F_{9, 75}=5.42$, $p<0.001$). There was no significant effect of test session or interaction. All pairwise multiple comparisons indicated that ketamine (10 and 15 mg/kg), betaine (20 and 30 mg/kg) and betaine (10, 20 and 30 mg/kg) pretreatment prior to ketamine (10 mg/kg) significantly decreased the duration of immobility. Furthermore, the mice with betaine (30 mg/kg) pretreatment prior to ketamine (10 mg/kg) had significantly shorter duration of immobility compared with the mice that received ketamine (10 mg/kg) alone.

Figure 3A:
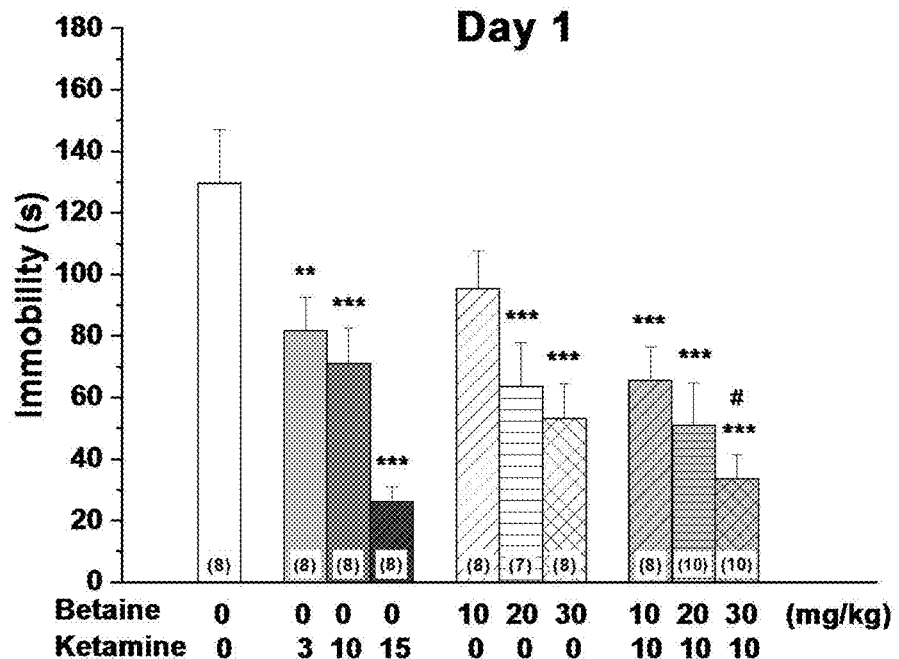
FIGS. 3A-3C show the effects of ketamine and betaine on the duration of immobility, struggling and swimming in FST. This experiment included groups with various doses of ketamine (3, 10, 15 mg/kg), betaine (10, 20, 30 mg/kg) and betaine (10, 20, 30 mg/kg) pretreatment prior to ketamine (fixed dose at 10 mg/kg). Tests were conducted on day 1 and 7 and the duration of immobility (A), struggling (B) and swimming (C) were recorded. All values are expressed as mean±SEM. *p<0.05, p<0.01, *p<0.001 vs. Saline/Saline, #p<0.05 vs. Saline/Ketamine.
Figure 3A:
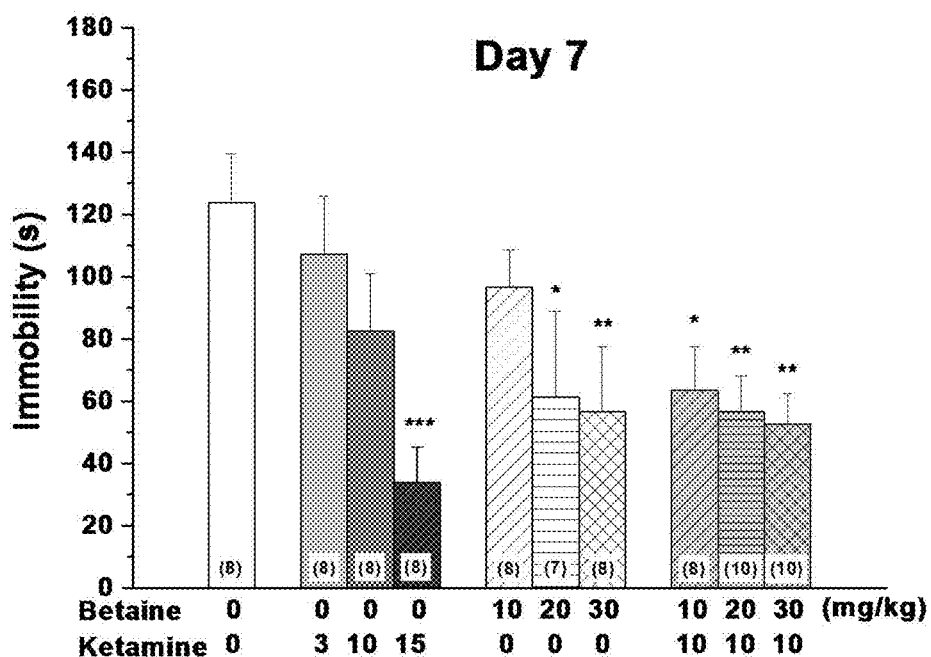

During day 1 test session, ketamine (3, 10 and 15 mg/kg), betaine (20 and 30 mg/kg), and betaine (10, 20 and 30 mg/kg) prior to ketamine (10 mg/kg) significantly reduced the duration of immobility compared with the vehicle control group. Further, the mice with betaine (30 mg/kg) pretreatment prior to ketamine (10 mg/kg) had significantly shorter duration of immobility compared with the mice that received ketamine (10 mg/kg) alone. During day 7 retest session, the duration of immobility in the groups of ketamine (15 mg/kg), betaine (20 and 30 mg/kg) and betaine (10, 20 and 30 mg/kg) pretreatment prior to ketamine (10 mg/kg) was significantly decreased compared with the vehicle control group (FIG. 3A).

Figure 3B:
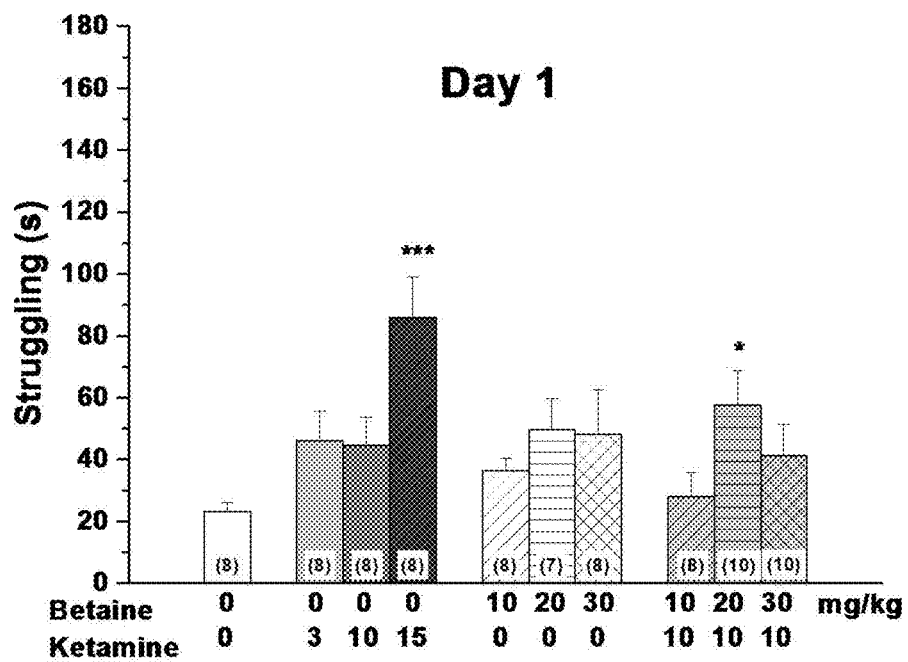
Figure 3B:
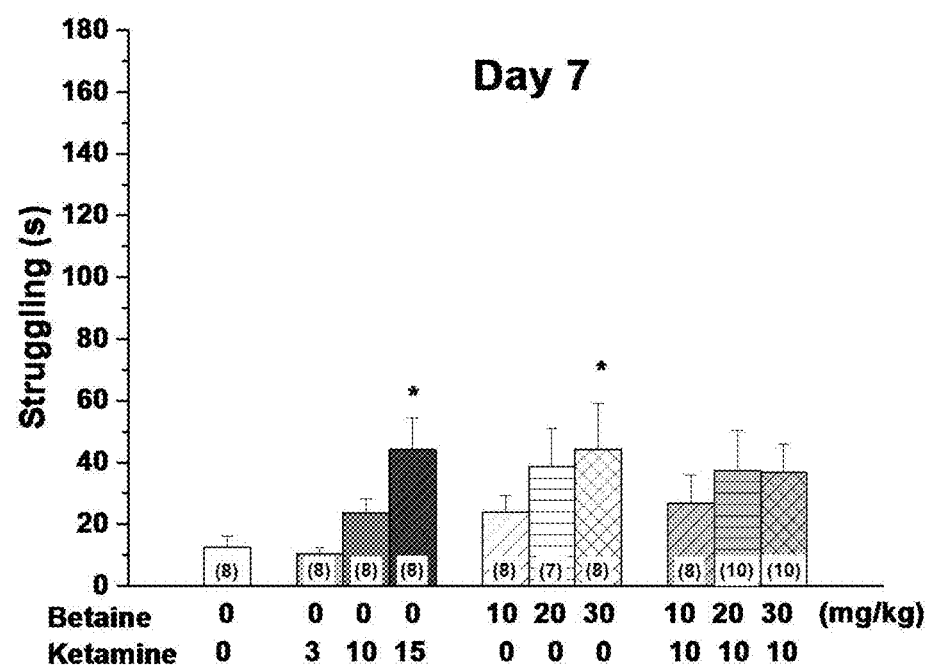

For the duration of struggling, a mixed-design ANOVA revealed significant main effects of treatment ($F_{9, 75}=2.586$, $p<0.05$) and test session ($F_{1, 75}=24.517$, $p<0.001$). All pairwise multiple comparisons indicated that ketamine (15 mg/kg), betaine (20 and 30 mg/kg), and betaine (20 mg/kg) prior to ketamine (10 mg/kg) significantly increased the duration of struggling. During day 1 test session, ketamine (15 mg/kg) and betaine (20 mg/kg) prior to ketamine (10 mg/kg) significantly increased the duration of struggling compared with control group. During day 7 retest session, ketamine (15 mg/kg) and betaine (30 mg/kg) significantly increased the duration of struggling compared with the control group (FIG. 3B).

Figure 3C:
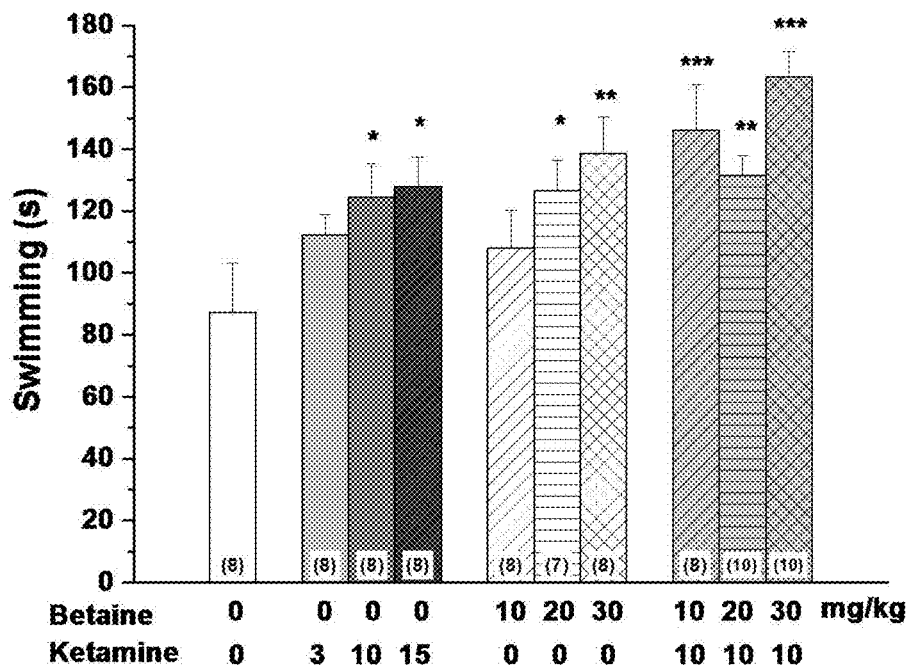
Figure 3C:
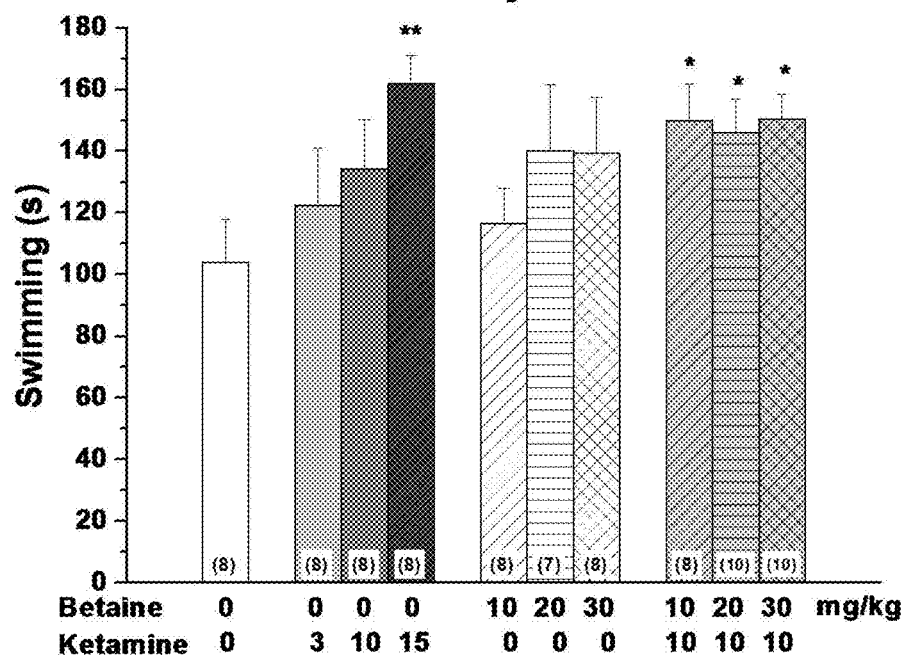

A mixed-design ANOVA revealed that there were significant effects of treatment ($F_{9, 75}=3.096$, $p<0.01$) and test session ($F_{1, 75}=4.978$, $p<0.05$) on the duration of swimming. All pairwise multiple comparisons demonstrated that the ketamine (10 and 15 mg/kg), betaine (20 and 30 mg/kg) and betaine (10, 20 and 30 mg/kg) pretreatment prior to ketamine (10 mg/kg) significantly increased the duration of swimming. During day 1 test session, betaine (20 and 30 mg/kg), ketamine (10 and 15 mg/kg) and betaine (10, 20 and 30 mg/kg) pretreatment prior to ketamine (10 mg/kg) significantly increased the duration of swimming compared with control group. Further, betaine (30 mg/kg) pretreatment prior to ketamine (10 mg/kg) group showed longer duration of swimming compared with ketamine (10 mg/kg). During day 7 retest session, ketamine (15 mg/kg) and betaine (10, 20 and 30 mg/kg) prior to ketamine (10 mg/kg) significantly increased the duration of swimming compared with control group (FIG. 3C).

Example 2

Betaine Antagonizes the Psychotomimetic Effect of Ketamine

Effects of Betaine and Ketamine on Motor Coordination in the Rotarod Test

Figure 4A:
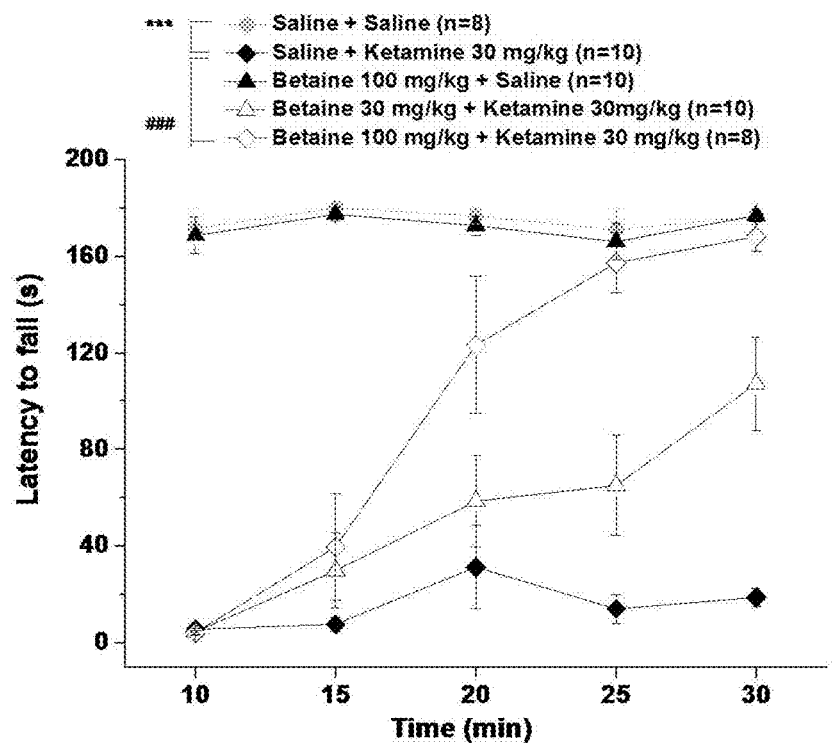
FIGS. 4A-4B show the effects of betaine on ketamine-induced motor in coordination in the rotarod test (A) and prepulse inhibition deficits in the acoustic startle reflex (B). Mice were pretreated with various doses of betaine (0, 30 and 100 mg/kg, i.p.). The latency to fall in the rotarod was recorded 10, 15, 20, 25 and 30 min after administration of ketamine (30 mg/kg, i.p.). PPI was measured. All values are expressed as mean±SEM. *p<0.05, ***p<0.001 vs. Saline/Saline, #p<0.05, ####p<0.001 vs. Saline/Ketamine.

In the experiment for assessing the effect of betaine and ketamine on rotarod performance, a mixed-design ANOVA revealed significant main effects of treatment ($F_{4, 205}=107.477$, $p<0.001$) and time ($F_{4, 205}=23.938$, $p<0.001$) on rotarod performance and a significant treatment×time interaction ($F_{16, 205}=8.48$, $p<0.001$). Post hoc multiple comparisons indicated that ketamine significantly decreased the latency to stay on the rotarod, and betaine (30 and 100 mg/kg) significantly reduced the ketamine-induced motor in coordination (FIG. 4A).

Effect of Betaine on Ketamine-Induced Prepulse Inhibition Deficits

Figure 4B:
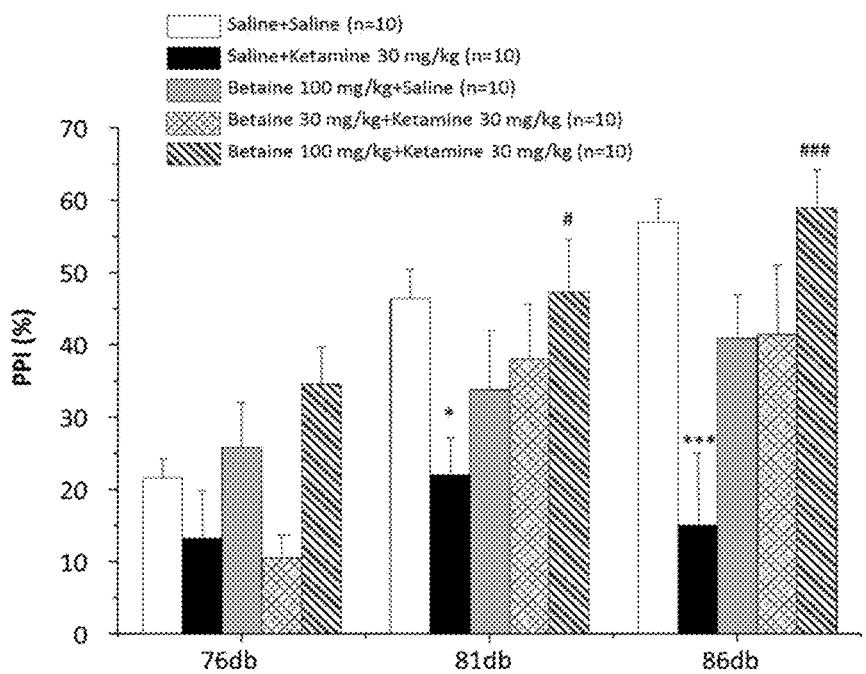

As for PPI, two-way ANOVA revealed a main effect of treatment ($F_{4,90}=5.338$, $p=0.001$), prepulse intensity ($F_{2,90}=27.215$, $p<0.001$) and a significant treatment×prepulse intensity interaction ($F_{8,90}=2.292$, $p<0.05$) were found. Ketamine alone significantly reduced the PPI but betaine prior to saline did not. Multiple comparisons revealed that pretreatment of betaine (100 mg/kg) significantly attenuated the ketamine-induced disruption of PPI (FIG. 4B).

Figure 5:
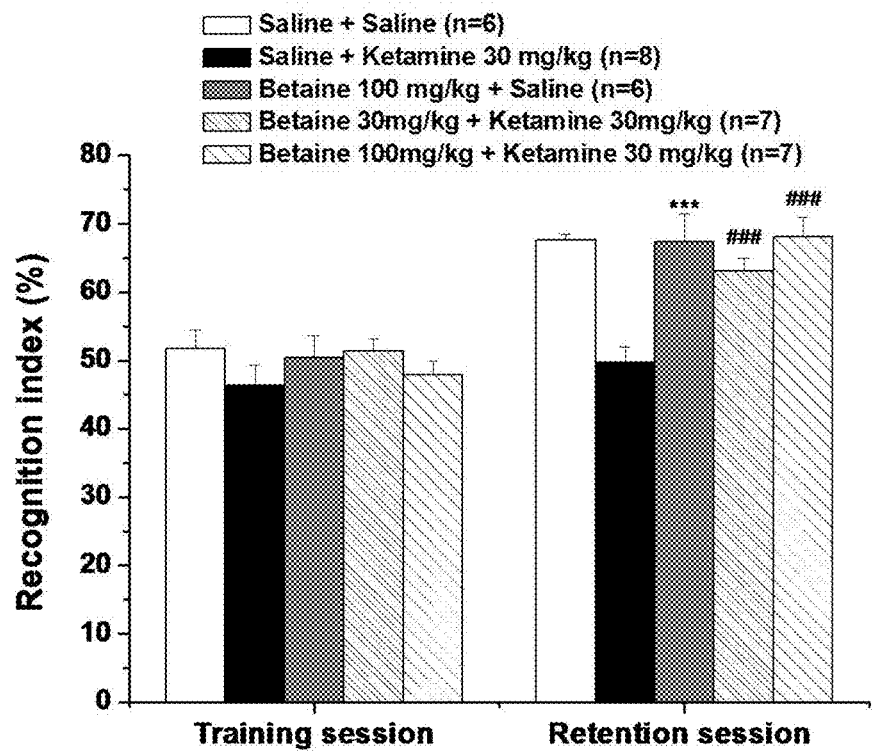
FIG. 5 shows the effects of betaine on ketamine-induced deficits in the novel object recognition test. Mice were pretreated with saline or betaine (30 and 100 mg/kg, i.p.) 30 min prior to ketamine (30 mg/kg). After 5 min, the training session in the novel object recognition test started. The retention session was conducted 24 h later. The amount of time spent exploring the novel object and total exploring time were measured. All values are expressed as mean±SEM. ***p<0.001 vs. Saline/Saline, #p<0.05, ####p<0.001 vs. Saline/Ketamine.

Effects of Betaine on Ketamine-Induced Recognition Memory Deficits in the Novel Object Recognition Test A mixed designed ANOVA revealed significant main effects of treatment ($F_{4, 29}=7.114$, $p<0.001$) and session ($F_{1, 29}=72.776$, $p<0.001$) and a significant treatment×session interaction ($F_{4, 29}=3.684$, $p<0.05$). There was no significant difference in the recognition index between treatment groups in the training session. Post hoc tests revealed that ketamine significantly reduced the recognition index and betaine (30 and 100 mg/kg) significantly reversed the recognition impairing effects of ketamine in the retention session (FIG. 5).

Effects of Betaine on Ketamine-Induced Social Withdrawal

Figure 6:
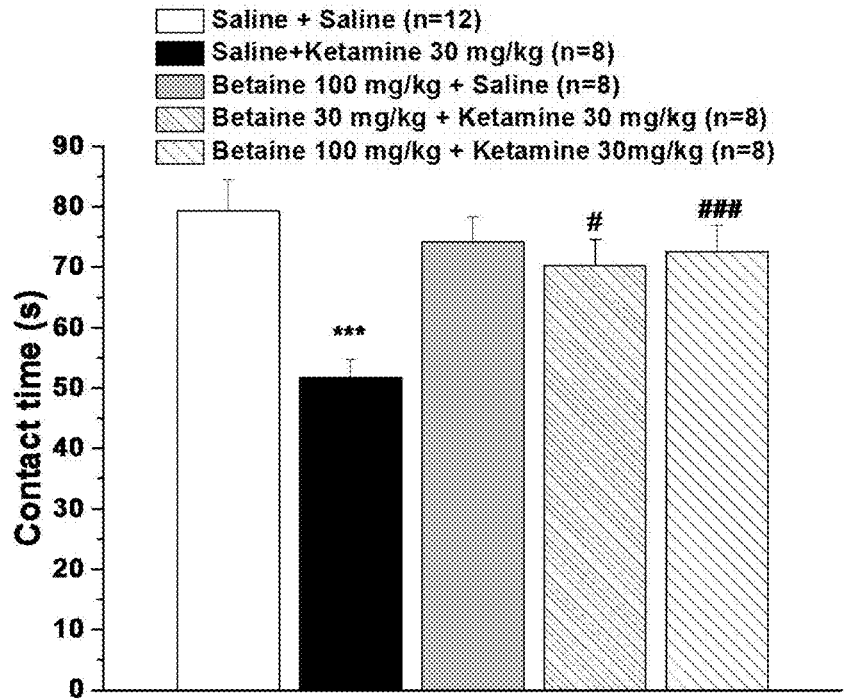
FIG. 6 shows the effects of betaine on ketamine-induced deficits in the social interaction test. For social interaction test, two mice with the same treatment but from different cages were introduced into testing arena. The total time that a pair spent in social interaction were recorded. All values are expressed as mean±SEM. ***p<0.001 vs. p<0.001 vs. Saline/Ketamine.

One-way ANOVA indicated a significant effect of treatment (total duration: $F_{4,39}=6.608$, $p<0.001$). Post hoc tests indicated that betaine (30 and 100 mg/kg, i.p.) significantly attenuated the reduction in social interaction duration induced by ketamine (FIG. 6).

Effects of Betaine on Ketamine-Induced Loss of Righting Reflex

Figure 7A:
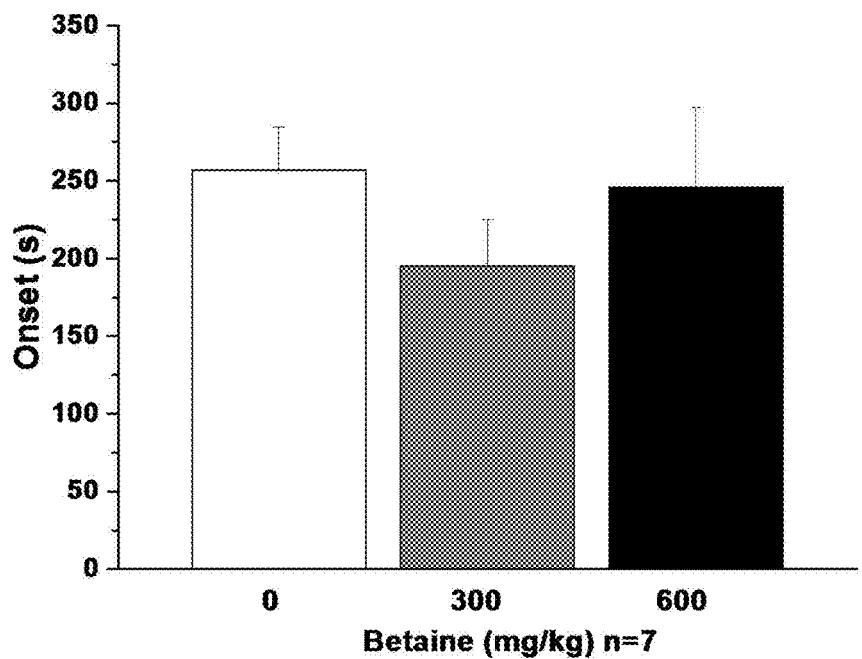
FIGS. 7A-7B show the effects of betaine on ketamine-induced loss of righting reflex. Mice were treated with betaine (0, 300 or 600 mg/kg) 30 min prior to anesthetic dose of ketamine (100 mg/kg).
Figure 7B:
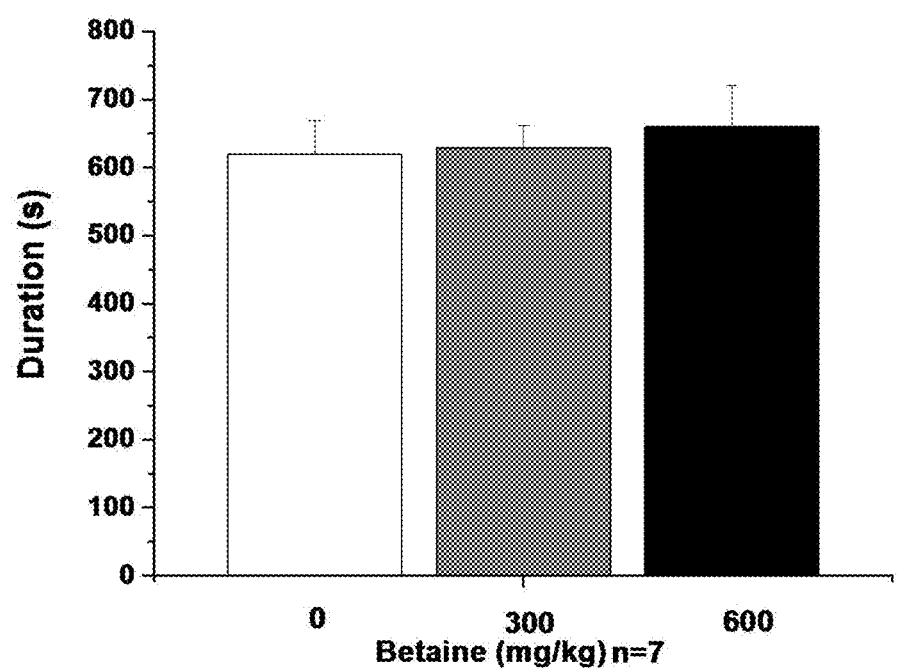

Ketamine (100 mg/kg, i.p.) produced LORR. One-way ANOVA revealed that pretreatment with betaine (300 and 600 mg/kg) did not affect the onset ($F_{2,18}=0.76$, $p=0.482$) and duration ($F_{2, 18}=0.191$, $p<0.828$) of ketamine-induced loss of righting reflex (FIG. 7).

Figure 8A:
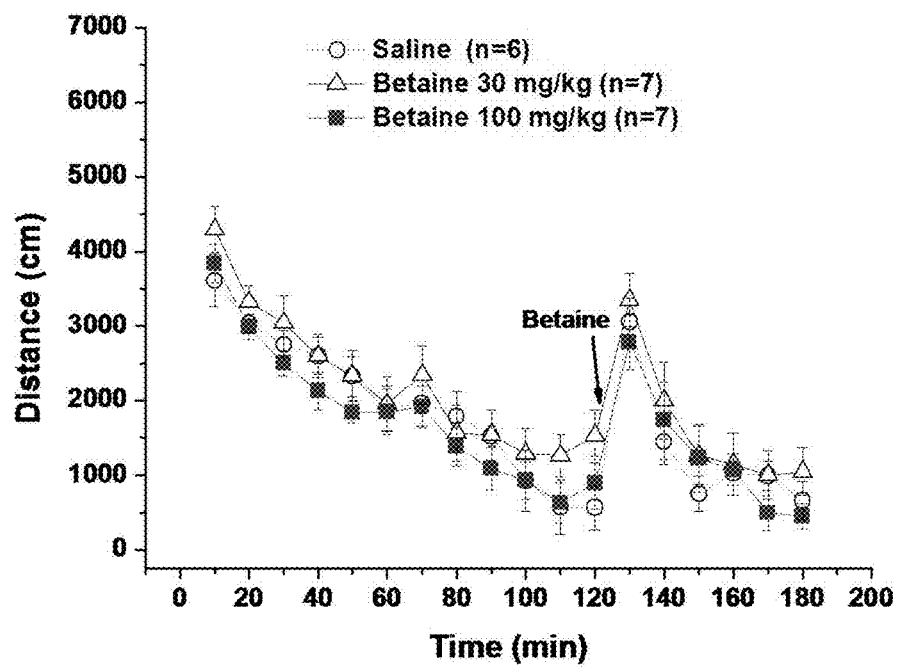
FIGS. 8A-8D show the effects of betaine on locomotor activity in the open field test and locomotor hyperactivity induced by ketamine. Spontaneous locomotor activity was recorded for 2 hours, then betaine (0, 30 and 100 mg/kg, i.p.) were administered and the distance moved (FIG. 8A) and the time in center (FIG. 8B) were recorded for 60 min. The effect of betaine on ketamine-induced locomotor hyperactivity was examined by administration of ketamine (30 mg/kg) 30 min after betaine (0, 30 and 100 mg/kg, i.p.) injection (FIG. 8C). Total distances after ketamine administration were measured for 30 min (FIG. 8D). All values are expressed as the mean±SEM. *p<0.05, **p<0.01, compared with Saline/Saline.
Figure 8B:
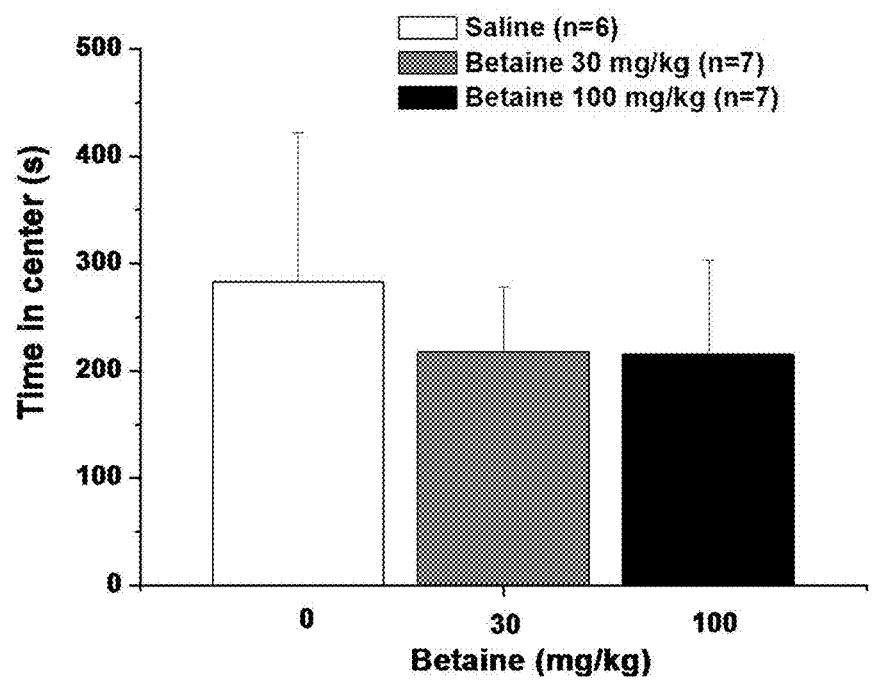
Figure 8C:
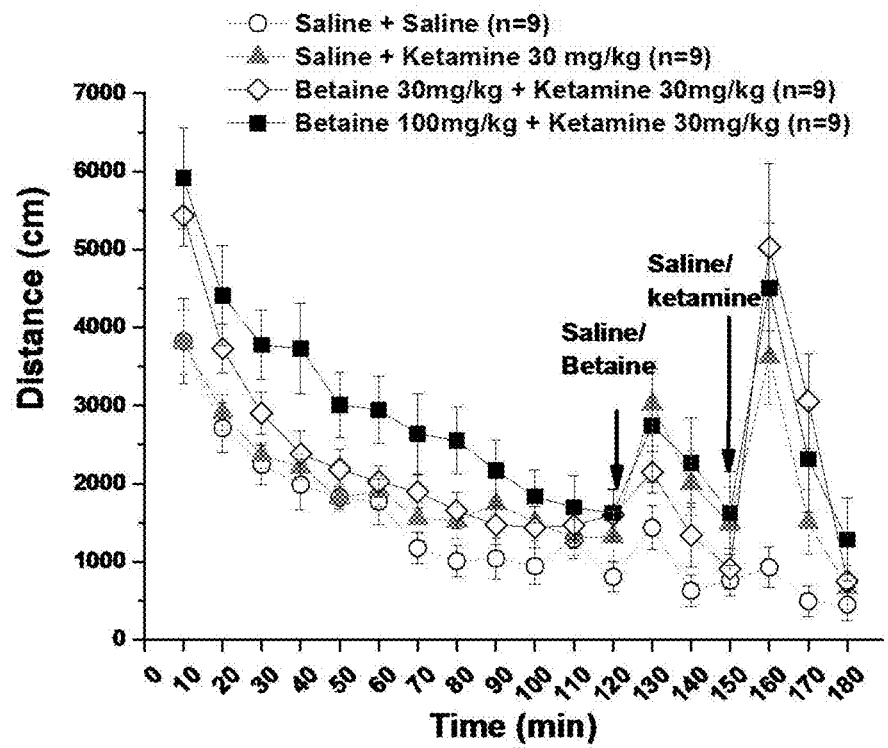
Figure 8D:
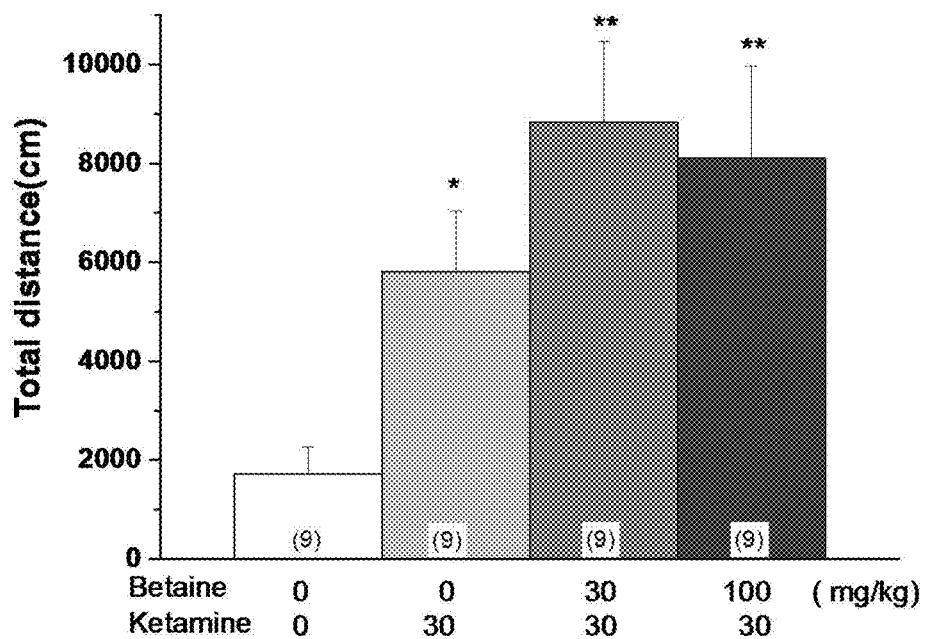

Effects of Betaine on Locomotor Activity and Locomotor Hyperactivity Induced by Ketamine One-way ANOVA revealed that betaine (30 and 100 mg/kg) did not affect the travel distances ($F_{2, 17}=0.862$, $p=0.44$) (FIG. 8A) and the time in center ($F_{2, 17}=0.149$, $p=0.863$) after betaine administration (FIG. 8B). The effect of betaine on ketamine-induced locomotor hyperactivity was examined by administration of ketamine (30 mg/kg) 30 min after betaine (0, 30 and 100 mg/kg, i.p.) injection. (FIG. 8C). One-way ANOVA demonstrated that there was a significant effect of treatment ($F_{3,32}=5.157$, $p<0.01$) on the total travel distances after ketamine administration (FIG. 8D). Post hoc tests indicated ketamine increased the total travel distances, while the ketamine-induced locomotor hyperactivity was not affected by betaine (30 and 100 mg/kg) treatment.

Example 3

DMG Produced Additive Antidepressant-Like Effects with Ketamine

Effects of Ketamine and DMG on the Duration of Immobility in FST

Figure 9:
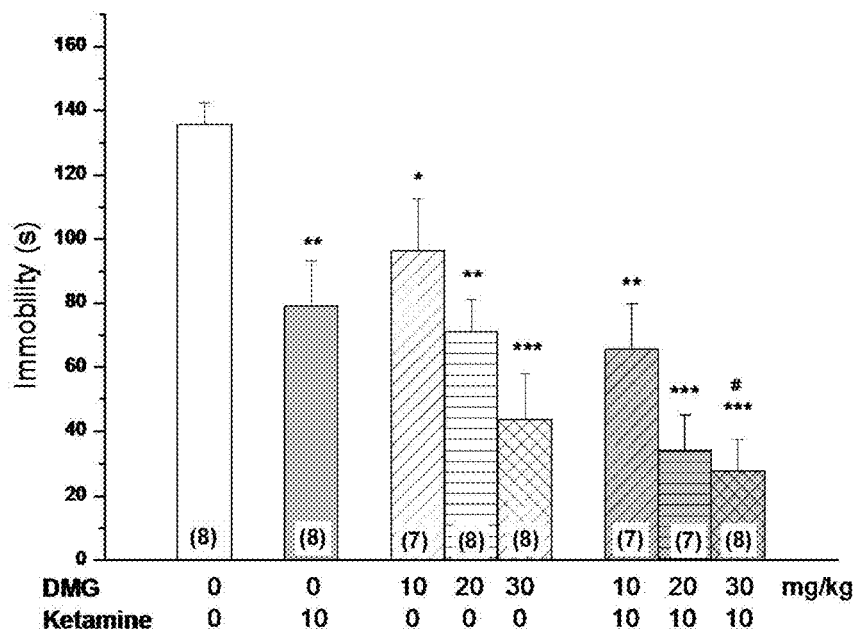
FIG. 9 shows the effects of ketamine and DMG on the duration of immobility in FST. Mice received the pre-test on day 1 for 15 min. The next day, DMG (0, 10, 20, or 30 mg/kg) was given 30 min prior to saline or ketamine (10 mg/kg). Thirty min after ketamine administration, mice were retested for 6 min and the duration of immobility during the last 4 min was recorded. All values are expressed as mean±SEM (n=7-8/group). The number of mice used is shown within parentheses. *p<0.05, p<0.01, *p<0.001 vs. Saline/Saline, #p<0.05 vs. Saline/Ketamine.

The duration of immobility was shown in FIG. 9. One-way ANOVA revealed that there was a significant main effect of treatment on the duration of immobility ($F_{7, 53}=8.094$, $p<0.001$). The Student-Newman-Keuls post hoc test indicated that ketamine (10 mg/kg), DMG (10, 20 and 30 mg/kg) and DMG (10, 20 and 30 mg/kg) pretreatment prior to ketamine (10 mg/kg) significantly decreased the duration of immobility. Furthermore, the mice with DMG (30 mg/kg) pretreatment prior to ketamine (10 mg/kg) had significantly shorter duration of immobility compared with the mice that received ketamine (10 mg/kg) alone. These results indicated that DMG alone exhibited antidepressant-like effects in the forced swim test and produced additive effects when combined with ketamine.

Example 4

Figure 10:
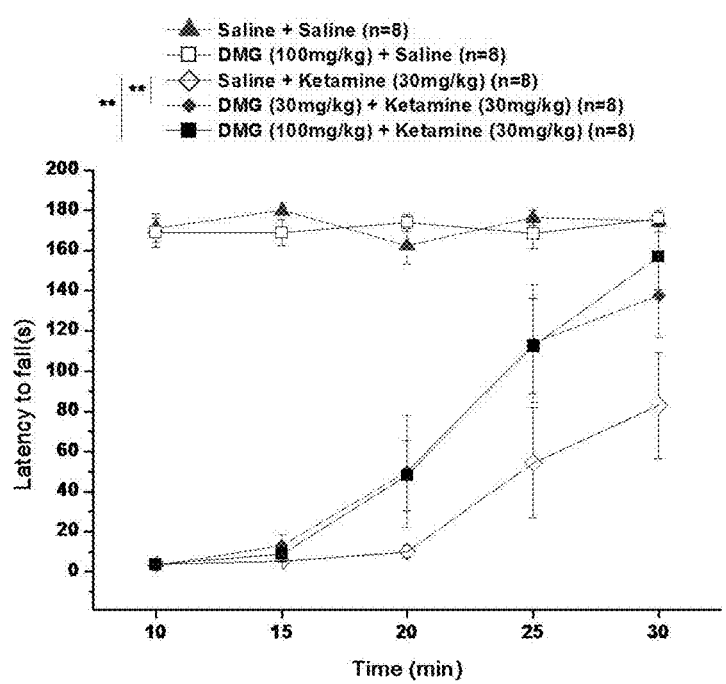
FIG. 10 shows the effects of DMG on ketamine-induced motor in coordination in rotarod test. Mice were pretreated with vehicle or DMG (30 and 100 mg/kg). The latency to fall in the rotarod was recorded 10, 15, 20, 25 and 30 min after administration of saline or ketamine (30 mg/kg). All values are expressed as mean±SEM (n=8/group). *p<0.05 compared with Saline/Ketamine.

DMG Significantly Attenuated Ketamine-Induced Psychotomimetic Behavioral Responses Effects of DMG and Ketamine on Motor Coordination in the Rotarod Test In the experiment for assessing the effect of DMG and ketamine on motor coordination, two-way repeated ANOVA revealed significant main effects of treatment ($F_{4, 140}=49.628$, $p<0.001$) and time ($F_{4, 140}=37.928$, $p<0.001$) and treatment×time interaction ($F_{16, 140}=6.988$, $p<0.001$) on rotarod performance. The Student-Newman-Keuls post hoc test indicated that ketamine significantly decreased the latency to stay on the rotarod, and DMG (30 and 100 mg/kg) significantly reduced ketamine-induced motor in coordination (FIG. 10).

Effects of DMG on Ketamine-Induced Prepulse Inhibition Deficits

Figure 11:
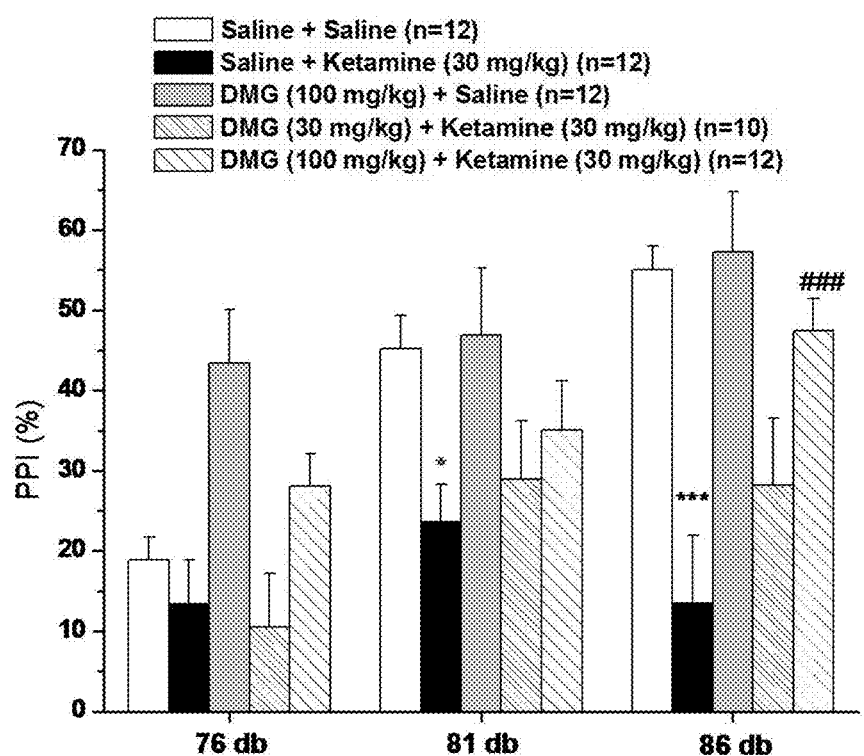
FIG. 11 shows the effects of DMG on ketamine-induced impairment in the acoustic startle reflex of prepulse inhibition. Mice were pretreated with vehicle or DMG (30 and 100 mg/kg) 30 min prior to saline or ketamine (30 mg/kg) administration. PPI was measured. All values are expressed as mean±SEM (n=10-12/group). *p<0.05, ***p<0.001 compared with Saline/Saline. ####p<0.001, vs. Saline/Ketamine.

FIG. 11 shows the effects of DMG on ketamine-induced prepulse inhibition deficits. Two-way repeated ANOVA demonstrated a main effect of treatment ($F_{4, 106}=7.989$, $p<0.001$) and prepulse intensity ($F_{2, 106}=19.288$, $p<0.001$) and a significant treatment×prepulse intensity interaction ($F_{8, 106}=2.812$, $p<0.01$). The Student-Newman-Keuls post hoc test revealed that ketamine reduced the PPI ($p<0.01$) and DMG (100 mg/kg) pretreatment significantly attenuated the ketamine-induced disruption of PPI ($p<0.001$).

Effects of DMG on Ketamine-Induced Locomotor Hyperactivity

Figure 12A:
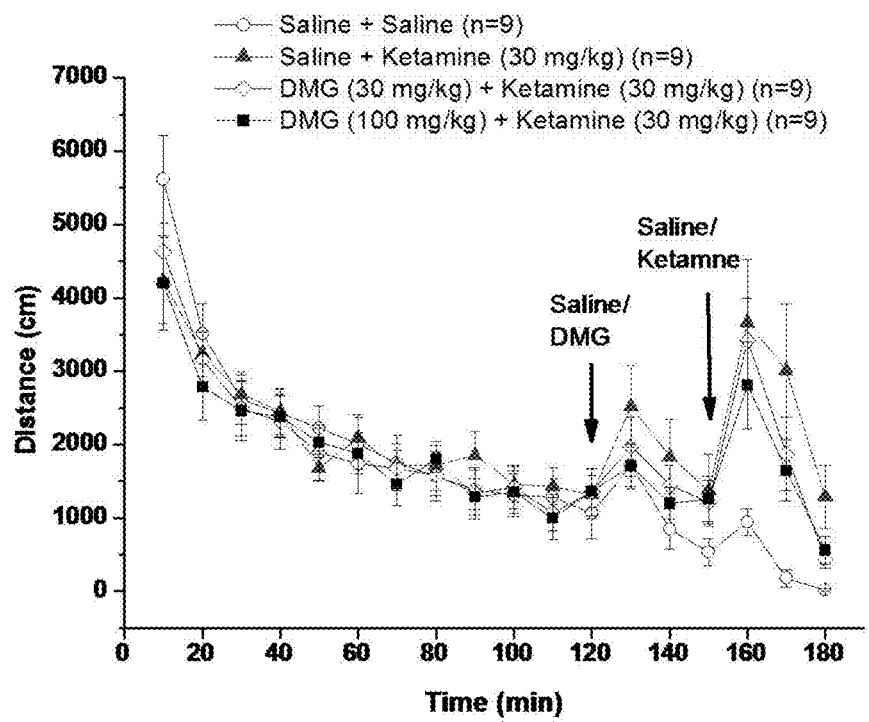
FIGS. 12A-12B show the effects of DMG on ketamine-induced locomotor hyperactivity.
Figure 12B:
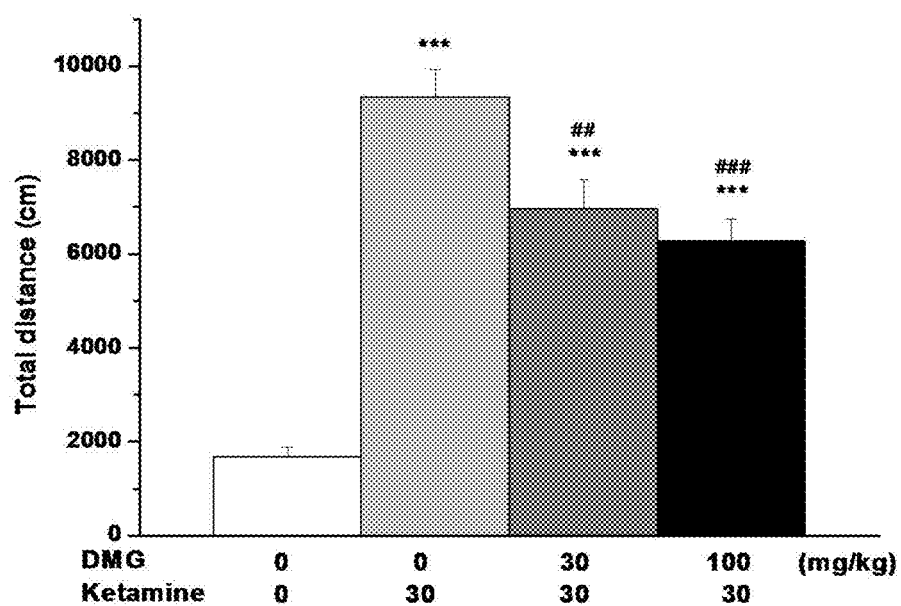

Locomotor activity was monitored for 180 min (FIG. 12A). After 120 min habituation in the testing chamber, DMG was given 30 min prior to ketamine. The total travelled distance after administration of ketamine (30 mg/kg) was measured for 30 min. FIG. 12B shows the total travelled distance after ketamine administration. One-way ANOVA demonstrated that there was a significant effect of treatment ($F_{3, 32}=40.53$, $p<0.001$). Post hoc test indicated that ketamine increased the travelled distance and the ketamine-induced locomotor hyperactivity was reduced by DMG (30 and 100 mg/kg) pretreatment.

Figure 13:
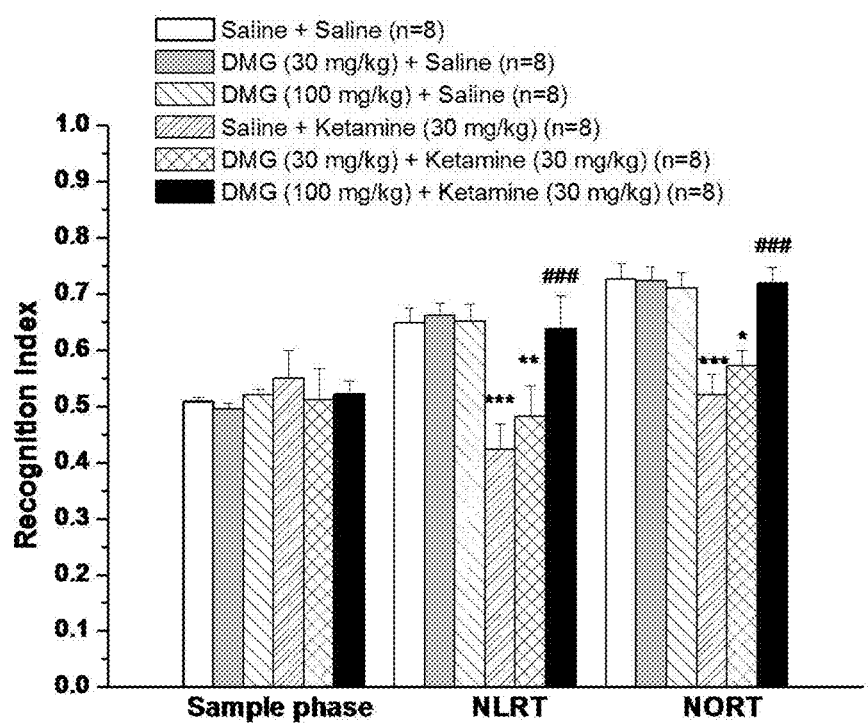
FIG. 13 shows the effects of DMG on ketamine-induced deficits in the novel location and novel object recognition tests. Mice were pretreated with DMG (0, 30 and 100 mg/kg) 30 min prior to saline or ketamine (30 mg/kg). The novel location and novel object recognition test sessions were conducted 30 min and 24 h after the sample phase. The amount of time spent exploring the novel location and novel object and total exploring time were measured. All values are expressed as mean±SEM (n=8/group). *p<0.05, p<0.01, *p<0.001 vs. Saline/Saline, ####p<0.001 vs. Saline/Ketamine.

Effects of DMG on Ketamine-Induced Recognition Memory Deficits in the Novel Location and Novel Object Recognition Test Two-way repeated ANOVA revealed significant main effects of treatment ($F_{5, 84}=9.155$, $p<0.001$) and test phase ($F_{2, 84}=25.106$, $p<0.001$) and a significant treatment×testing phase interaction ($F_{10, 84}=3.331$, $p=0.001$). The Student-Newman-Keuls post hoc test revealed that DMG pretreatment (100 mg/kg) significantly attenuated ketamine-induced recognition memory impairment in both NLRT and NORT (FIG. 13).

Effects of DMG on Ketamine-Induced Loss of Righting Reflex

Figure 14A:
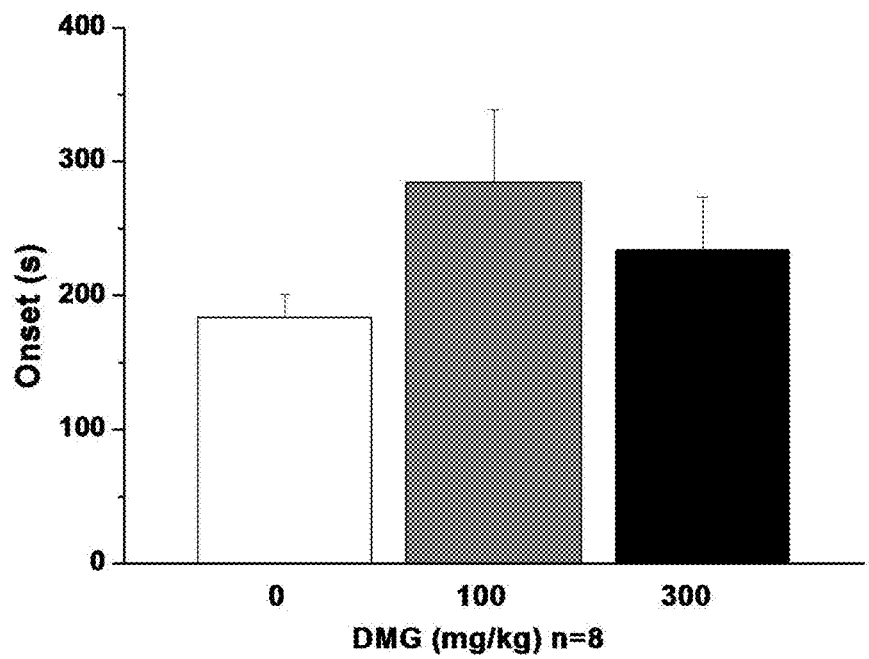
FIGS. 14A-14B show the effects of DMG on ketamine-induced loss of righting reflex. Mice were pretreated with DMG (0, 100 or 300 mg/kg) 30 min prior to anesthetic dose of ketamine (100 mg/kg). The latency (FIG. 14A) and the duration (FIG. 14B) of loss of righting reflex were recorded. All values are expressed as the mean±SEM (n=8/group).
Figure 14B:
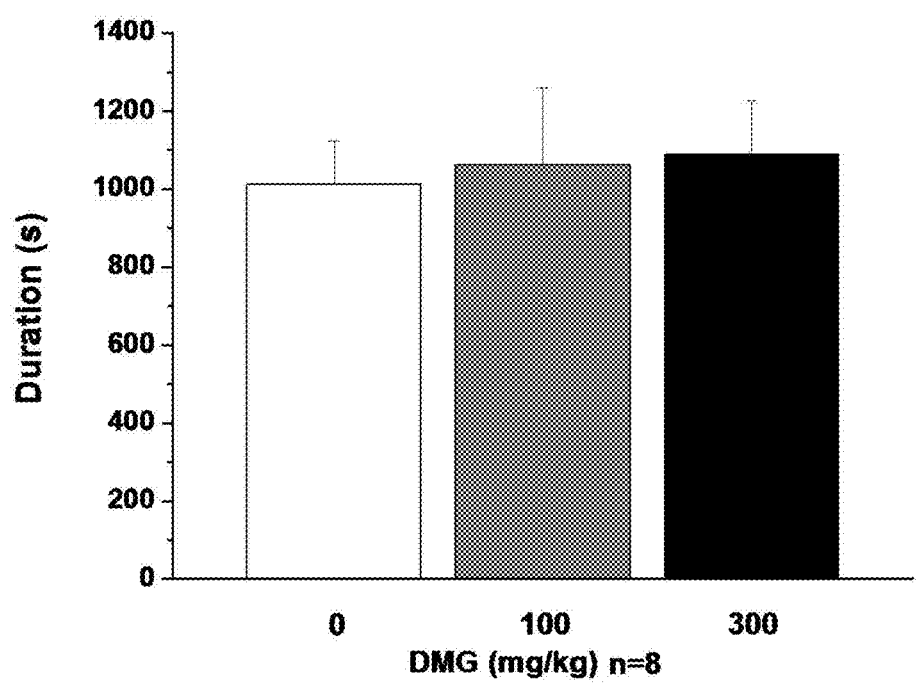

Ketamine (100 mg/kg, i.p.) produced a loss of righting reflex. One-way ANOVA revealed that pretreatment with DMG (100 and 300 mg/kg) did not affect onset ($F_{2, 21}=1.572$, $p=0.231$) and duration ($F_{2, 21}=0.0636$, $p<0.939$) of ketamine-induced loss of righting reflex (FIG. 14A, 14B).

The results described above demonstrate that DMG exhibited antidepressant-like effect and had additive effect in combination with ketamine. Moreover, DMG reversed ketamine-induced psychotomimetic-like behaviors, but did not affect the anesthetic effect of ketamine.

In conclusion, the present invention demonstrated that a methyl glycine derivative with partial agonist activity at glycine site of NMDA receptors, such as betaine and DMG, exhibits antidepressant-like effect and had additive effect in combination with ketamine. Moreover, the methyl glycine derivative reversed ketamine-induced psychotomimetic-like behaviors, but did not affect the anesthetic effect of ketamine. Based on the distinct effects of betaine and DMG on ketamine-induced behavioral responses, the possibility of methyl glycine derivative to cause the pharmacokinetic changes in ketamine metabolism is extremely low. It appears that methyl glycine derivatives have differential effects on behavioral responses elicited by ketamine at different dose levels. As a nutrient supplement, betaine and DMG are generally considered safe and nontoxic. The disclosure of present invention suggests a new indication for methyl glycine derivatives to treat schizophrenia and depression, especially, schizophrenic patients with depression. Moreover, the methyl glycine derivatives can be potentially used as an adjunct to reduce the psychotomimetic side effect of ketamine for patients with treatment-resistant depression.

Example 5

Betaine and its Metabolite DMG Prevented or Treated Addictive Disorders of Ketamine The dose-dependent effects of betaine and its metabolite DMG on ketamine addiction were evaluated by the intravenous self-administration (IVSA) paradigm under a progressive ratio (PR) schedule. Animals were implanted indwelling catheters flushing of ketamine (0.5 mg/kg/per infusion), termed the training dose, under a FR1 schedule during daily 3-h sessions. After acquisition of stable responding for ketamine (criterion of less than 20% deviation from the mean of the total number of reinforcers earned in three consecutive sessions for each rat), the ketamine reinforcement schedule was changed to FR2 and maintained until responding stabilized at least for 3 days. Then, the PR schedule was conducted. The lever presses required to gain an infusion was determined by: $5 \times e^{(infusion\ number \times 0.2)} - 5$ (i.e., 1, 2, 4, 6, 9, 2, 15, 20, 25, 32, etc). The PR schedule will be terminated automatically if animals did not gain another infusion within an hour. The dose-dependent effects of betaine of self-administration of various doses of ketamine (0.1-0.5 mg/kg/per infusion) and the effect of DMG (30 mg/kg) on self-administration of ketamine (0.3 mg/kg/per infusion) were assessed by pretreatment 30 min prior to their daily operant session using a within-subject Latin square design.

Figure 15:
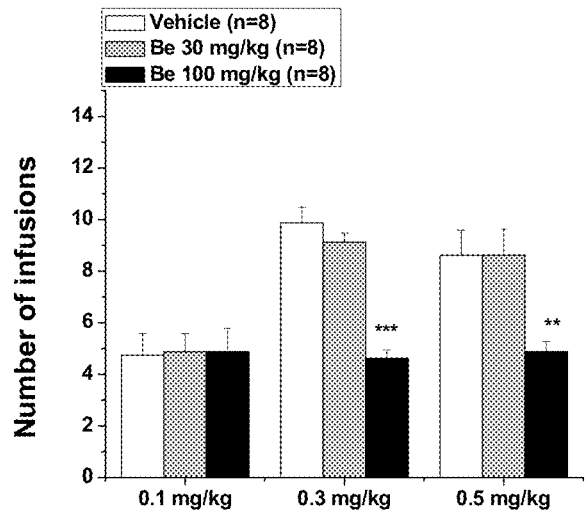
FIG. 15 shows the effect of betaine pretreatment on ketamine self-administration (SA) over a range of doses (0.1-0.5 mg/kg) under a PR schedule. A Latin-square design was used. Rats were pretreated with betaine (0, 30 and 100 mg/kg). The infusion number, break points and lever-press responses were recorded. All values are expressed as mean±SEM (n=8/group). *p<0.05, p<0.01, *p<0.001 compared with the vehicle group.
Figure 15:
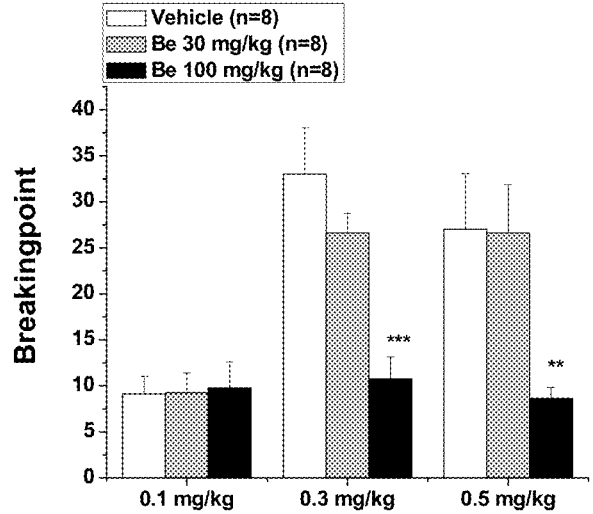
Figure 15:
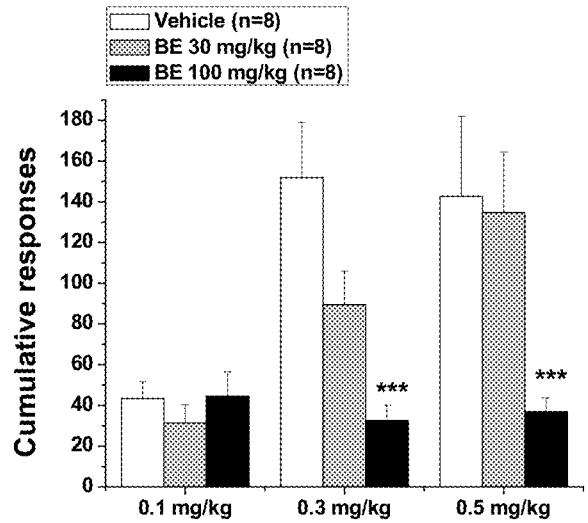
Figure 16:
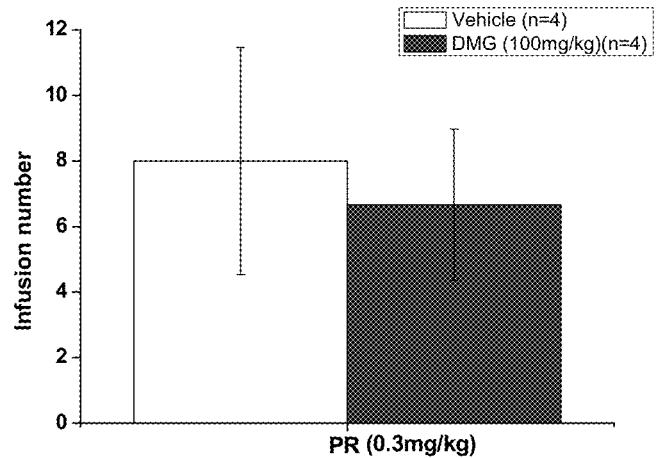
FIG. 16 shows the effect of DMG (100 mg/kg) pretreatment on the ketamine (0.3 mg/kg) self-administration under a PR schedule. A Latin-square design was used. Rats were pretreated with DMG (0 and 100 mg/kg). The infusion number, break points and lever-press responses were recorded. All values are expressed as mean±SEM (n=4/group).
Figure 16:
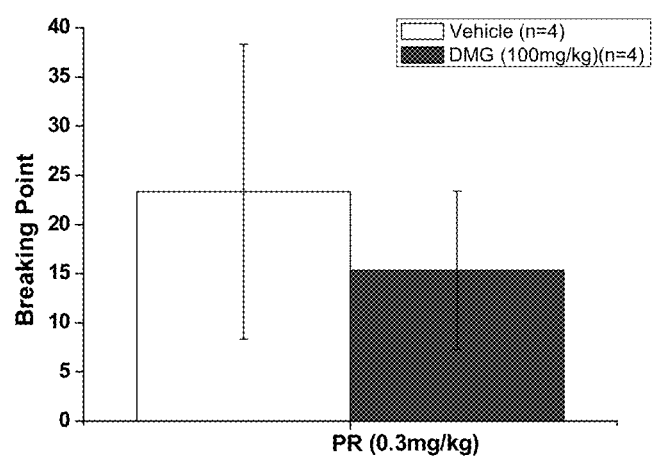
Figure 16:
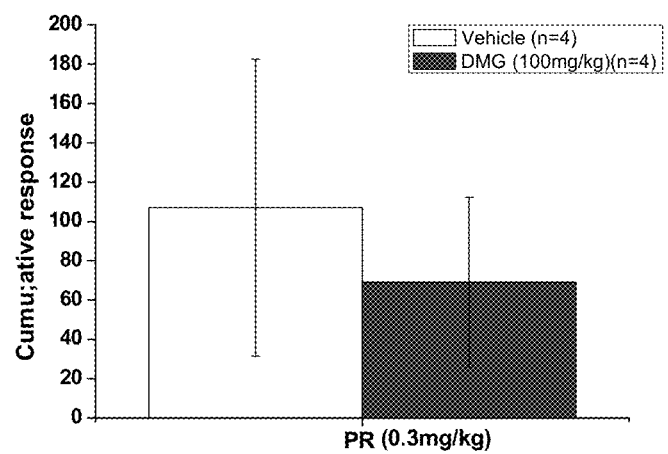

The results were shown in FIG. 15 and FIG. 16. A two-way repeated-measures ANOVA revealed significant main effects of ketamine ($F_{2, 28}=15.231$, $p<0.001$) and betaine ($F_{2, 28}=16.596$, $p<0.001$) and significant interaction between ketamine and betaine ($F_{4, 28}=4.093$, $p<0.01$). There was an increase in ketamine consumption over the dose-response curve in the control (vehicle-treated) animals. IVSA of ketamine was dose-dependently reduced by betaine pretreatment, with a significant effective dose of 30 mg/kg and a 3-5 times reduction at 100 mg/kg tested (FIG. 15). IVSA of ketamine also revealed that pretreatment with DMG (100 mg/kg) reduced 40% of cumulative responses by ketamine (FIG. 16). The pretreatments of betaine and DMG significantly decreased the ketamine self-administration under PR schedule, suggesting that betaine and its metabolite DMG could exhibit a potential of preventing or treating ketamine addiction.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. An antidepressant composition, comprising ketamine in an effective amount of treating depression and betaine in an effective amount of preventing or treating an addictive disorder or reducing the psychotomimetic side effect of ketamine.

2. The composition of claim 1, wherein the composition is in an amount for treating depressive symptoms in a patient with schizophrenia.

3. The composition of claim 1, wherein betaine is in an effective amount of antagonizing a psychotomimetic side effect of ketamine.

4. The composition of claim 1, wherein the composition is in an effective amount for preventing or treating treatment-resistant depression.

5. A method for treating depression in a subject in need thereof, comprising administering an effective amount of an antidepressant composition of claim 1 to the subject.

6. The method of claim 5, wherein the subject is a schizophrenic patient with depression.

7. The method of claim 5, wherein the subject is a patient with treatment-resistant depression.

8. The method of claim 5, wherein the subject is a patient with ketamine addictive disorders.

* * * * *